(12) United States Patent
Li et al.

(10) Patent No.: US 7,368,445 B2
(45) Date of Patent: May 6, 2008

(54) FUSED PYRAZOLE DERIVATIVES AS TGF-β SIGNAL TRANSDUCTION INHIBITORS FOR THE TREATMENT OF FIBROSIS AND NEOPLASMS

(75) Inventors: Hong-Yu Li, Zionsville, IN (US); William Thomas McMillen, McCordsville, IN (US); Yan Wang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/597,979

(22) PCT Filed: Feb. 16, 2005

(86) PCT No.: PCT/US2005/004812

§ 371 (c)(1),
(2), (4) Date: Aug. 15, 2006

(87) PCT Pub. No.: WO2005/092894

PCT Pub. Date: Oct. 6, 2005

(65) Prior Publication Data

US 2007/0155722 A1    Jul. 5, 2007

Related U.S. Application Data

(60) Provisional application No. 60/548,910, filed on Mar. 1, 2004.

(51) Int. Cl.
   *C07D 487/04* (2006.01)
   *A61K 31/517* (2006.01)
(52) U.S. Cl. ............ 514/217.05; 544/105; 544/284; 544/354; 540/484; 514/217.06; 514/217.09; 514/230.5; 514/249; 514/266.21
(58) Field of Classification Search ............ 540/484; 544/105, 284, 354; 514/217.06, 217.05, 514/217.09, 230.5, 249, 266.21
See application file for complete search history.

(56) References Cited

FOREIGN PATENT DOCUMENTS

| WO | WO 01/62756 | 8/2001 |
| WO | WO 02/094833 | 11/2002 |
| WO | WO 03/097639 | 11/2003 |
| WO | WO 2004/050659 | 6/2004 |

*Primary Examiner*—Kahsay T Habte
(74) *Attorney, Agent, or Firm*—Danica Hostettler; Tina M. Tucker

(57) ABSTRACT

The disclosed invention is directed to compounds of the formula: Formula (I) and methods of using these compounds.

(I)

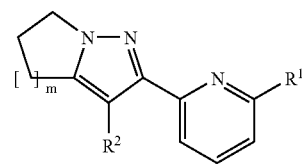

11 Claims, No Drawings

FUSED PYRAZOLE DERIVATIVES AS TGF-β SIGNAL TRANSDUCTION INHIBITORS FOR THE TREATMENT OF FIBROSIS AND NEOPLASMS

This is the national phase application, under 35 USC 371, for PCT/US2005/004812, filed 16 Feb. 2005, which claims the benefit, under 35 USC 119(e), of US provisional application 60/548,910, filed 1 Mar. 2004.

The invention relates to new compounds and their use as pharmaceutical agents, in particular their use as TGF-β signal transduction inhibitors.

BACKGROUND OF THE INVENTION

The transforming growth factor-beta (TGF-beta) ("TGF-β") polypeptides influence growth, differentiation, and gene expression in many cell types. The first polypeptide of this family that was characterized, TGF-β1, has two identical 112 amino acid subunits that are covalently linked. TGF-β1 is a highly conserved protein with only a single amino acid difference distinguishing humans from mice. There are two other members of the TGF-β gene family that are expressed in mammals. TGF-β2 is 71% homologous to TGF-β1 (de Martin, et al. (1987) EMBO J. 6:3673-3677), whereas TGF-β3 is 80% homologous to TGF-β1 (Derynck, et al. (1988) EMBO J. 7:3737-3743). There are at least three different extracellular TGF-β receptors, Type I, II and III that are involved in the biological functions of TGF-β1, -β2 and -β3 (For reviews, see Derynck (1994) TIBS 19:548-553 and Massague (1990) Ann. Rev. Cell Biol. 6:597-641). The Type I and Type II receptors are transmembrane serine/threonine kinases that in the presence of TGF-β form a heteromeric signaling complex (Wrana, et al (1992) Cell 71: 1003-1014).

The mechanism of activation of the heteromeric signaling complex at the cell surface has been elucidated (Wrana, et al. (1994) Nature 370: 341-347). TGF-β first binds the type II receptor that is a constitutively active transmembrane serine/threonine kinase. The type I receptor is subsequently recruited into the complex, phoshorylated at the GS domain and activated to phosphorylate downstream signaling components (e.g. Smad proteins) to initiate the intracellular signaling cascade. A constitutively active type I receptor (T204D mutant) has been shown to effectively transduce TGF-β responses, thus bypassing the requirement for TGF-β and the type II receptor (Wieser, et al. (1995) EMBO J. 14: 2199-2208). Although no signaling function has been discovered for the type III receptor, it does increase the affinity of TGF-β2 for the type II receptor making it essentially equipotent with TGF-β1 and TGF-β3 (Lopez-Casillas, et al. (1993) Cell 73: 1435-1444).

Vascular endothelial cells lack the Type III receptor. Instead endothelial cells express a structurally related protein called endoglin (Cheifetz, et al. (1992) J. Biol. Chem. 267:19027-19030), which only binds TGF-β1 and TGF-β3 with high affinity. Thus, the relative potency of the TGF-β's reflects the type of receptors expressed in a cell and organ system. In addition to the regulation of the components in the multi-factorial signaling pathway, the distribution of the synthesis of TGF-β polypeptides also affects physiological function. The distribution of TGF-β2 and TGF-β3 is more limited (Derynck, et al. (1988) EMBO J. 7:3737-3743) than TGF-β1, e.g., TGF-β3 is limited to tissues of mesenchymal origin, whereas TGF-β1 is present in both tissues of mesenchymal and epithelial origin.

TGF-β1 is a multifunctional cytokine critical for tissue repair. High concentrations of TGF-β1 are delivered to the site of injury by platelet granules (Assoian and Sporn (1986) J. Cell Biol. 102:1217-1223). TGF-β1 initiates a series of events that promote healing including chemo taxis of cells such as leukocytes, monocytes and fibroblasts, and regulation of growth factors and cytokines involved in angiogenesis, cell division associated with tissue repair and inflammatory responses. TGF-β1 also stimulates the synthesis of extracellular matrix components (Roberts, et al. (1986) Proc. Natl. Acad. Sci. USA 83:4167-4171; Sporn, et al. (1983) Science 219:1329-1330; Massague (1987) Cell 49:437-438) and most importantly for understanding the pathophysiology of TGF-β1, TGF-β1 autoregulates its own synthesis (Kim, et al. (1989) J. Biol. Chem. 264:7041-7045).

The compounds disclosed herein may also exhibit other kinase activity, such as p38 kinase inhibition and/or KDR (VEGFR2) kinase inhibition. Assays to determine such kinase activity are known in the art and one skilled in the art would be able to test the disclosed compounds for such activity.

The compounds disclosed and claimed in this patent application are generally related to compounds disclosed and claimed in PCT patent application number PCT/US002/11884, filed 13 May 2002, which claims priority from U.S. patent application U.S. Ser. No. 60/293,464, filed 24 May 2001, and is herein incorporated by reference.

SUMMARY OF THE INVENTION

A compound of the formula:

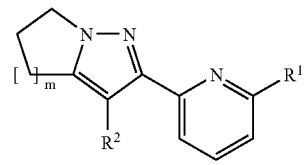

Formula I wherein $R^1$ is hydrogen or $(C_1-C_6)$ alkyl;
$R^2$ is selected from the group consisting of:

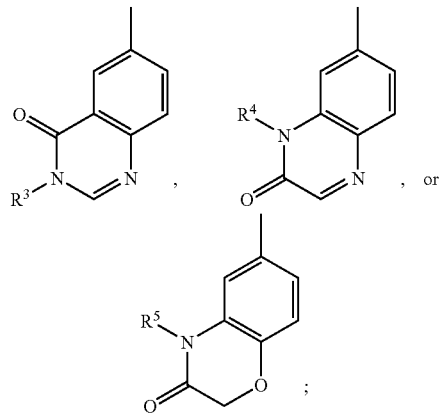

$R^3$ is $(C_1-C_6)$alkyl, or $(CH_2)_nX$;
$R^4$ is $(C_1-C_6)$alkyl, or $(CH_2)_nX$;
$R^5$ is hydrogen, $(C_1-C_6)$alkyl, or $(CH_2)_nX$;
X is selected from the group consisting of a halogen, $NR^aR^b$, N-morpholino, N-piperidine, N-pyrrolidine, or N-azepane;
n is an integer from 1-4;
m is an integer from 1-3;

$R^a$ and $R^b$ are each independently hydrogen or $(C_1-C_6)$alkyl;
and the pharmaceutically acceptable salts thereof.

A preferred embodiment of the invention is the compound wherein
m is 1;
$R^1$ is methyl;
$R^2$ is

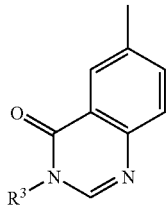

$R^3$ is methyl;
and the pharmaceutically acceptable salts thereof.

DETAILED DESCRIPTION OF THE INVENTION

The term "effective amount" as used in "an effective amount of a compound of Formula I," for example, refers to an amount of a compound of the present invention that is capable of inhibiting TGF-β signal transduction.

The general chemical terms used herein have their usual meanings. For example, as used herein, the term "$C_1-C_4$ alkyl", alone or in combination, denotes a straight-chain or branched-chain $C_1-C_4$ alkyl group consisting of carbon and hydrogen atoms, examples of which are methyl, ethyl, propyl, isopropyl, butyl, sec-butyl, tert-butyl, and the like.

As used herein, the term "halo" or "halogen" represents fluorine, chlorine, bromine, or iodine. The term "hydroxy," alone or in combination, represents an —OH moiety. The term "carboxy" or "carboxyl" refers to a carboxylic acid. The term "carboxamide" refers to a carbonyl substituted with an —$NH_2$ moiety. The term "oxo" refers to a carbonyl group.

As used herein, the term "$C_1-C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1-C_6$ alkyl" includes within its definition the terms "$C_1-C_4$ alkyl" and "$C_1-C_3$ alkyl."

Abbreviations used herein include the following:
The term $Pd_2(dba)_3$ refers to tris(dibenzylideneacetone) dipalladium.
The term dppf refers to 1,1'-bis(diphenylphosphino) ferrocene.
The term DMAP=4-(N,N-dimethylamino)pyridine.
The term DMF refers to N,N-dimethylformamide.
The term DMSO refers to dimethylsulfoxide.
The term eq refers to equivalent.
The term ES refers to electron spray.
The term h refers to hour(s).
The term HPLC refers to high performance liquid chromatography.
The term L refers to liter.
The term min refers to minutes.
The term mL refers to milliliter.
The term mmol refers to millimole.
The term Mp refers to melting point.
The term MPLC refers to medium pressure liquid chromatography.
The term MS refers to mass spectrum.
The term THF refers to tetrahydrofuran.

The term THP refers to tetrahydropyran.
The term TLC refers to thin layer chromatography.
The term W refers to watts.

Compounds Exemplified in the Application Include the Following

It will be understood that the number preceding the compound name corresponds to the example wherein the compound is exemplified.
1) 3-methyl-6-[2-[6-methyl-(pyridin-2-yl)]-5,6-dihydro-4H-pyrrolo[1,2-b]pyrazol-3-yl]-3H-quinazolin-4-one
2) 1-methyl-7-[2-[6-methyl-(pyridin-2-yl)]-5,6-dihydro-4H-pyrrolo[1,2-b]pyrazol-3-yl]-1H-quinoxalin-2-one
3) 3-methyl-6-[2-(pyridin-2-yl)-5,6-dihydro-4H-pyrrolo[1,2-b]pyrazol-3-yl]-3H-quinazolin-4-one
4) 3-methyl-6-[2-[6-pentyl-(pyridin-2-yl)]-5,6-dihydro-4H-pyrrolo[1,2-b]pyrazol-3-yl]-3H-quinazolin-4-one
5) 6-[2-[6-Methyl-(pyridin-2-yl)]-5,6-dihydro-4H-pyrrolo[1,2-b]pyrazol-3-yl]-4H-benzo[1,4]oxazin-3-one
6) 3-(2-Chloro-ethyl)-6-[2-[6-methyl-(pyridin-2-yl)]-5,6-dihydro-4H-pyrrolo[1,2-b]pyrazol-3-yl]-3H-quinazolin-4-one
7) 6-[2-[6-methyl-(pyridin-2-yl)]-5,6-dihydro-4H-pyrrolo[1,2-b]pyrazol-3-yl]-3-(2-morpholin-4-yl-ethyl)-3H-quinazolin-4-one
8) 3-(2-Dimethylamino-ethyl)-6-[2-[6-methyl-(pyridin-2-yl)]-5,6-dihydro-4H-pyrrolo[1,2-b]pyrazol-3-yl]-3H-quinazolin-4-one
9) 6-[2-[6-Methyl-(pyridin-2-yl)]-5,6-dihydro-4H-pyrrolo[1,2-b]pyrazol-3-yl]-3-(2-piperidin-1-yl-ethyl)-3H-quinazolin-4-one
10) 6-[2-[6-Methyl-(pyridin-2-yl)]-5,6-dihydro-4H-pyrrolo[1,2-b]pyrazol-3-yl]-3-(2-pyrrolidin-1-yl-ethyl)-3H-quinazolin-4-one
11) 3-(2-Azepan-1-yl-ethyl)-6-[2-[6-methyl-(pyridin-2-yl)]-5,6-dihydro-4H-pyrrolo[1,2-b]pyrazol-3-yl]-3H-quinazolin-4-one
12) 7-[2-[6-Methyl-(pyridin-2-yl)]-5,6-dihydro-4H-pyrrolo[1,2-b]pyrazol-3-yl]-1-(2-pyrrolidin-1-yl-ethyl)-3,4-dihydro-1H-quinoxalin-2-one
13) 1-(2-Dimethylamino-ethyl)-7-[2-[6-methyl-(pyridin-2-yl)]-5,6-dihydro-4H-pyrrolo[1,2-b]pyrazol-3-yl]-3,4-dihydro-1H-quinoxalin-2-one and the pharmaceutically acceptable salts thereof.

The compounds exemplified above are merely representative of the invention and are not limiting in any fashion.

The compounds disclosed herein can be made according to the following schemes and examples. The examples should in no way be understood to be limiting in any way as to how the compounds may be made.

The skilled artisan will appreciate that the introduction of certain substituents will create asymmetry in the compounds of Formula (I). The present invention contemplates all enantiomers and mixtures of enantiomers, including racemates. It is preferred that the compounds of the invention containing chiral centers are single enantiomers.

The compounds of the present invention can be prepared by a variety of procedures, some of which are illustrated in the Schemes below. It will be recognized by one of skill in the art that the individual Steps in the following schemes may be varied to provide the compounds of Formula (I). The particular order of Steps required to produce the compounds of Formula (I) is dependent upon the particular compound being synthesized, the starting compound, and the relative lability of the substituted moieties.

SCHEME I:

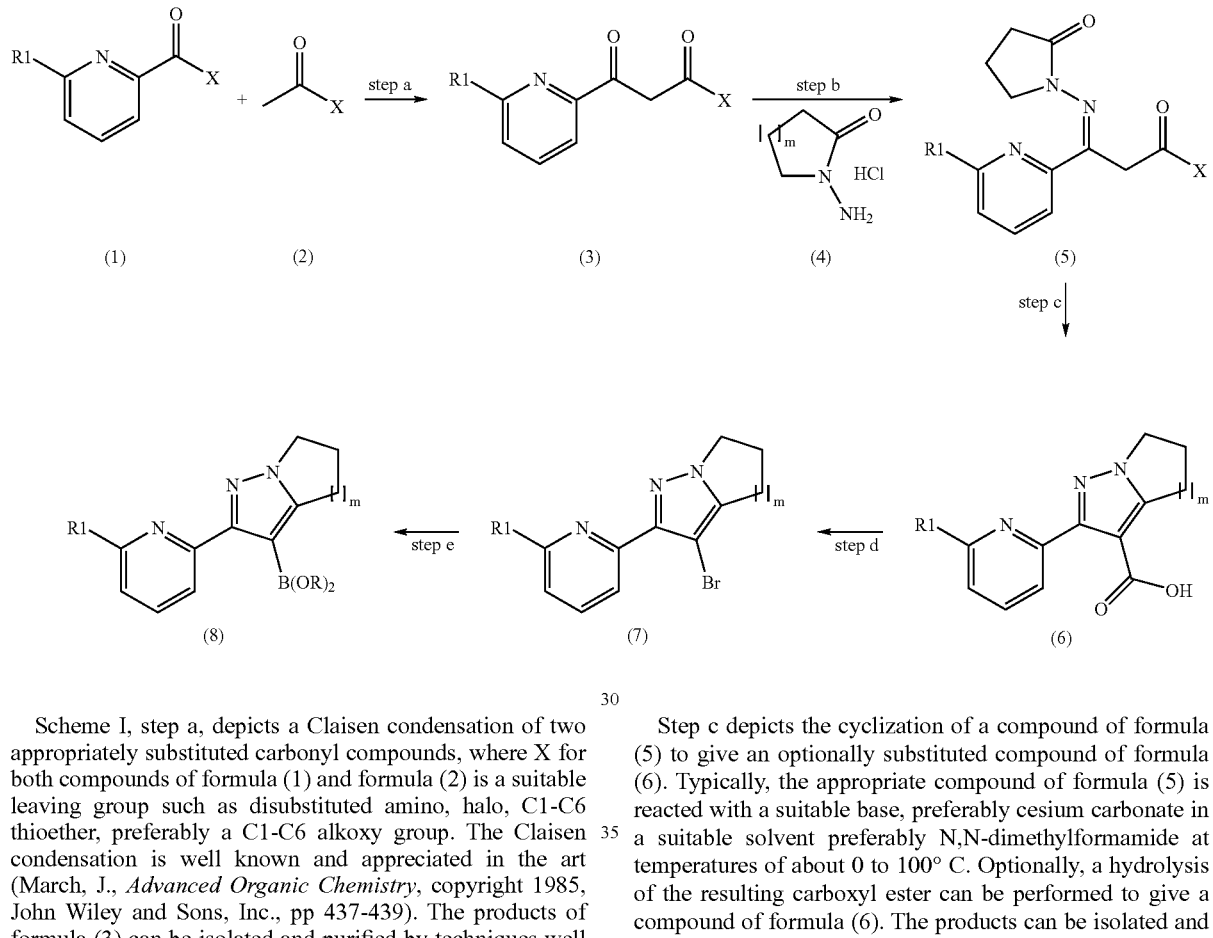

Scheme I, step a, depicts a Claisen condensation of two appropriately substituted carbonyl compounds, where X for both compounds of formula (1) and formula (2) is a suitable leaving group such as disubstituted amino, halo, C1-C6 thioether, preferably a C1-C6 alkoxy group. The Claisen condensation is well known and appreciated in the art (March, J., *Advanced Organic Chemistry*, copyright 1985, John Wiley and Sons, Inc., pp 437-439). The products of formula (3) can be isolated and purified by techniques well known in the art, such as precipitation, filtration, extraction, evaporation, trituration, chromatography, and recrystallization.

In Scheme I, step b, conditions can be applied to a compound of formula (3) with the appropriate compound of formula (4), to give a compound of formula (5). Typically, the reaction is carried out in a suitable solvent such as ethanol, N-methylpyrrolidin-2-one, or preferably pyridine. The reaction is carried out at temperatures of about 60° C. to ambient for 4-24 hours. The products can be isolated and purified by techniques described above.

Step c depicts the cyclization of a compound of formula (5) to give an optionally substituted compound of formula (6). Typically, the appropriate compound of formula (5) is reacted with a suitable base, preferably cesium carbonate in a suitable solvent preferably N,N-dimethylformamide at temperatures of about 0 to 100° C. Optionally, a hydrolysis of the resulting carboxyl ester can be performed to give a compound of formula (6). The products can be isolated and purified by techniques described above.

Step d depicts the transformation of a carboxylic acid, formula (6), to a halide of formula (7). This transformation is well known and appreciated in the art (Larock, R. C., *Comprehensive Organic Transformations*, $2^{nd}$ Ed., copyright 1999, John Wiley & Sons, pp 741-742).

Step e depicts the transformation of a heteroaryl halide, formula (7), to a heteroaryl boronic acid or ester formula (8). This transformation is well known and appreciated in the art (Li, Wenjie; Nelson, Dorian P. et al, *J. Org Chem*, 2002, 5394-5397).

SCHEME II:

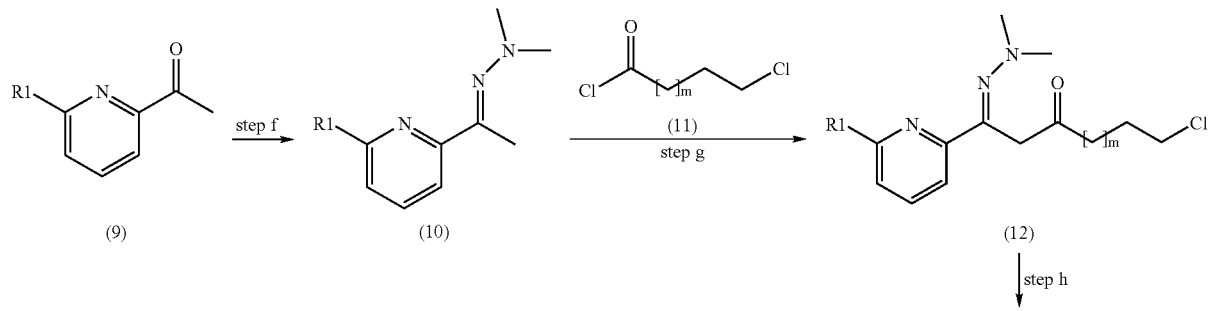

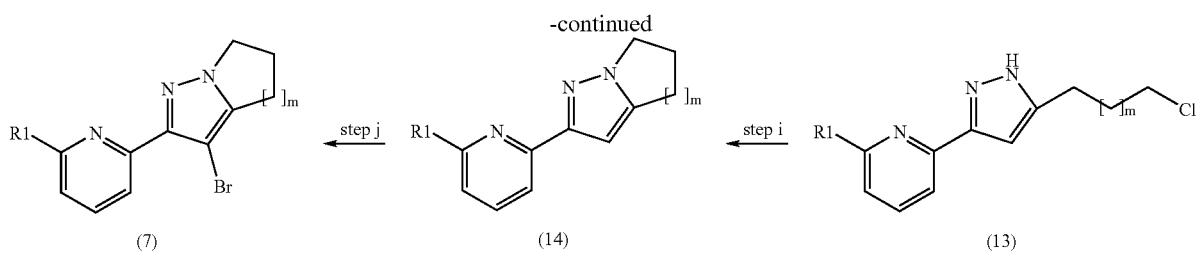

Scheme II depicts an alternative approach to the synthesis of the compound of formula (7). One skilled in the art would appreciate the conversion of various acetylpyridines of formula (9) to hydrazones of formula (10) through step f. This conversion is known in the art (*Org. Synth.* 1988, VI, pg 12, H. El Ouazzani, N. Khiar, I. Fernández, and F. Alcudia, *J. Org. Chem.* 1997, 62, 287-291).

Scheme II, step g depicts the acylation of a hydrazone compound of formula (10) with a compound of formula (11) to give the product of formula (12). Typically the compound of formula (10) is contacted with a suitable base, such as potassium bis(trimethylsilyl)amide, lithium bis(trimethylsilyl)amide, sodium bis(trimethylsilyl)amide, sodium hydride, lithium hydride, potassium hydride, sodium alkoxides (sodium methoxide, or sodium ethoxide) or potassium alkoxides (potassium methoxide, or potassium ethoxide), or preferably lithium diisopropylamine. Generally, the reaction is carried out in suitable solvents, such as tetrahydrofuran, toluene, or a combination of such, at temperatures of about −78° C. to ambient temperature. The product, formula (12), can be isolated and purified by techniques well known in the art, such as precipitation, filtration, extraction, evaporation, trituration, chromatography, and recrystallization or can be carried forward in Scheme II without purification.

Scheme II, step h, depicts the conversion of a beta-ketohydrazone of formula (12) to a substituted pyrazole of formula (13). Typically, a compound of formula (12) is treated with a source of hydrazine such as hydrazine, hydrazine monohydrate, hydrazine hydrate, or preferably hydrazine hydrochloride in an appropriate solvent such as tetrahydrofuran, ethanol, methanol, water, or preferable a combination of these at temperatures of about ambient temperature to refluxing. The product, formula (13), can be isolated and purified by techniques well known in the art, such as precipitation, filtration, extraction, evaporation, trituration, chromatography, and recrystallization.

Scheme II, step i, depicts the cyclization of a haloalkylpyrazole compound of formula (13) to a 5,6-dihydro-4H-pyrrolo[1,2-b]pyrazole of formula (14). Typically, the appropriate compound of formula (13) is reacted with a suitable base, preferably sodium hydride in a suitable solvent, preferably N,N-dimethylformamide, at temperatures of about 0 to 100° C. The products of formula (14) can be isolated by methods described above.

Scheme II, step j, depicts the halogenation of a compound of formula (14) to give a compound of formula (7). Typically the appropriate compound of formula (14) is contacted with a halogenating agent such as N-chlorosuccinamide, N-iodosuccinamide, chlorine, bromine, iodine, or preferably N-bromosuccinamide, in an appropriate solvent such as dichoromethane, chloroform, benzene, or preferably N,N-dimethylformamide, at temperatures of about 0 to 50° C.

SCHEME III:

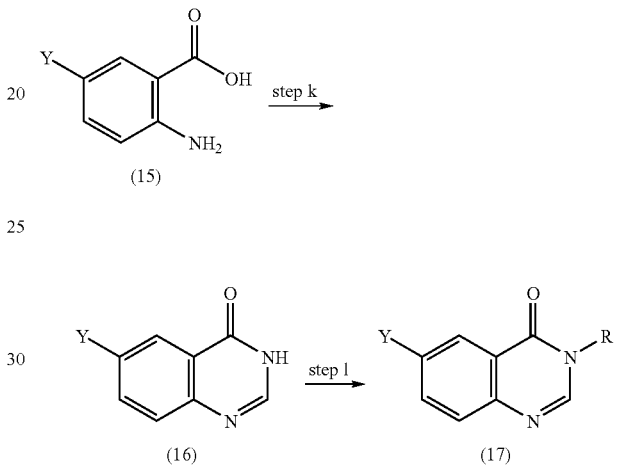

Scheme III, step k, depicts the conversion of an optionally substituted aminobenzoic acid of formula (15) to an optionally substituted quinazolin-4-one of formula (16), where Y can be an appropriate leaving group such as a halide. This transformation is known in the art (Ronald A. LeMahieu et al., *J. Med. Chem.,* 1983, 26(3), 420-5). Typically, the aminobenzoic acids of formula (15) are contacted with formamide at temperatures from ambient temperature to refluxing. The product of formula (16) can be isolated by methods described above.

Scheme III, step 1, depicts the alkylation of a compound of formula (16) to an optionally substituted compound of formula (17). Typically, a compound of formula (16) is contacted with a suitable alkylating agent in the presence of a suitable base, such as potassium bis(trimethylsilyl)amide, lithium diisopropylamine, lithium bis(trimethylsilyl)amide, sodium bis(trimethylsilyl)amide, lithium hydride, potassium hydride, sodium alkoxides (sodium methoxide, or sodium ethoxide) or potassium alkoxides (potassium methoxide, or potassium ethoxide), or preferably sodium hydride. Generally, the reaction is carried out in suitable solvents, such as tetrahydrofuran, or preferably N,N-dimethylformamide, at temperatures of about −78° C. to ambient temperature. The product, formula (17), can be isolated and purified by techniques well known in the art, such as precipitation, filtration, extraction, evaporation, trituration, chromatography, and recrystallization.

SCHEME IV:

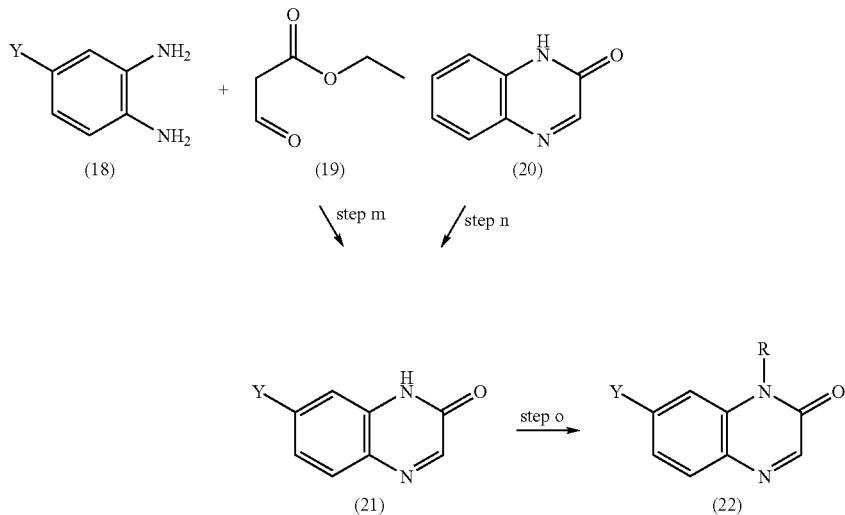

Scheme IV, step m, depicts the conversion of a optionally substituted 1,2-diamino benzene of formula (18) to an optionally substituted quinoxalin-2-one of formula (21). This transformation is known in the art (Linda, P. and Marino, G. Ric. Sci. Rend., Ser. A. 1963, 3, 225; Lumma, W. C. et al. J. Med. Chem. 1981, 24, 93-101; Ping Chen, et al., Tet. Let. 2001, 42, 4293-4295). Typically, a compound of formula (18) is contacted with an alkylglyoxalate of formula (19) in a suitable solvent such as methanol, butanol, isopropanol, or preferably ethanol at temperatures of 120° C. to ambient temperature for 1 to 24 hours. The product of formula (21) can be purified by methods described above. Alternatively, the compound of formula (21) can be synthesized by the method of step n. Typically, a compound of formula (20) is contacted with an appropriate halogenating agent such as N-chlorosuccinamide, N-iodosuccinamide, chlorine, iodine, or preferably bromine in an appropriate solvent such as dichloromethane, chloroform, benzene, N,N-dimethylformamide, or preferably acetic acid at temperatures of about 0 to 50° C.

Scheme IV, step o, depicts the alkylation of a compound of formula (21) to an optionally substituted compound of formula (22). Typically, a compound of formula (21) is contacted with a suitable alkylating agent in the presence of a suitable base, such as potassium bis(trimethylsilyl)amide, lithium diisopropylamine, lithium bis(trimethylsilyl)amide, sodium bis(trimethylsilyl)amide, lithium hydride, potassium hydride, sodium alkoxides (sodium methoxide, or sodium ethoxide) or potassium alkoxides (potassium methoxide, or potassium ethoxide), or preferably sodium hydride. Generally, the reaction is carried out in suitable solvents, such as tetrahydrofuran, or preferably N,N-dimethylformamide, at temperatures of about −78° C. to ambient temperature. The product, formula (22), can be isolated and purified by techniques well known in the art, such as precipitation, filtration, extraction, evaporation, trituration, chromatography, and recrystallization.

SCHEME V:

Scheme V, step p, depicts the conversion of a quinoxalin-2-one of formula (21) to a 2-chloroquinoxaline of formula (23). Typically, a compound of formula (21) is contacted with an appropriate dehydrating halogenation agent such as phosphorous pentachloride, thionyl chloride, or preferably phosphorus oxychloride with or without a suitable solvent such as chloroform, dichloromethane, benzene, toluene, but preferably without solvent.

Scheme V, step q, depicts the displacement of a chloroquinoxaline of formula (23) to give an alcohol of formula (24). Typically, a compound of formula (23) is contacted with ethylene glycol in the presence of a suitable base such as potassium bis(trimethylsilyl)amide, lithium diisopropylamine, lithium bis(trimethylsilyl)amide, sodium bis(trimethylsilyl)amide, lithium hydride, potassium hydride, sodium alkoxides (sodium methoxide, or sodium ethoxide) or potassium alkoxides (potassium methoxide, or potassium ethoxide), or preferably sodium hydride in a suitable solvent such as tetrahydrofuran, or preferably N,N-dimethylformamide, at temperatures of about −50° C. to ambient temperature. The product, formula (24), can be isolated and purified by techniques well known in the art, such as precipitation, filtration, extraction, evaporation, trituration, chromatography, and recrystallization.

SCHEME VI:

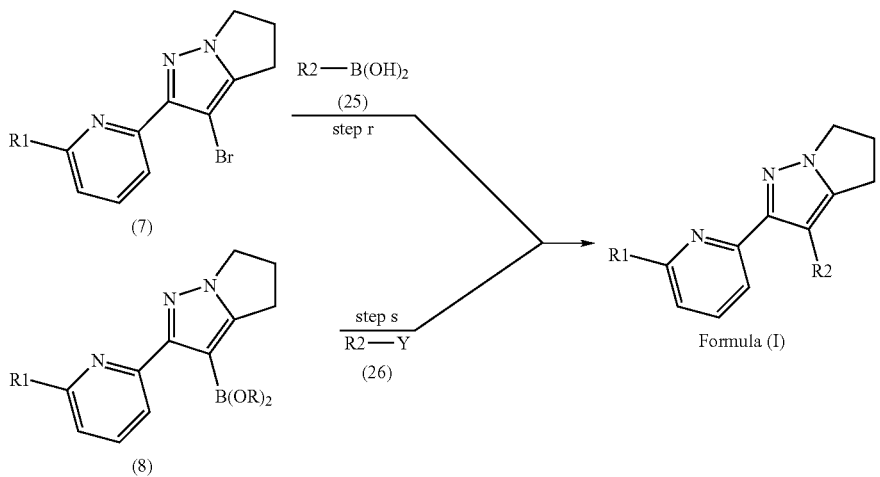

Scheme VI, step r, depicts the palladium catalyzed coupling of a compound of formula (7) with a compound of formula (25) to give a compound of the invention (Formula I). Typically, the halide of formula (7) is used as a leaving group in combination with a compound of formula (25) in the presence of a suitable catalyst, preferably tetrakis(triphenylphosphine)palladium(0), and a suitable base such as sodium carbonate, to further give compounds of Formula (I) (Suzuki reaction see: Miryaura, N.; Yanagi, T.; Suzuki, A. The Palladium-Catalyzed Cross Coupling Reaction of Phenylboronic Acid with Haloarenes in the Presence of Bases. *Synth. Commun.*, 1981, 513-518). The compounds of formula (25) produced by methods known in the art (Li, Wenjie; Nelson, Dorian P. et al, *J. Org. Chem*, 2002, 5394-5397). In the same way, a compound of formula (8) can be used in combination with a compound of formula (26), where Y can be an appropriate leaving group such as a halide, in the presence of a suitable palladium catalyst, preferably tetrakis(triphenylphosphine)palladium(0), and a suitable base such as potassium carbonate to further give compounds of Formula (I) (Suzuki reaction see: Miryaura, N.; Yanagi, T.; Suzuki, A. The Palladium-Catalyzed Cross Coupling Reaction of Phenylboronic Acid with Haloarenes in the Presence of Bases. *Synth. Commun.*, 1981, 513-518).

SCHEME VI:

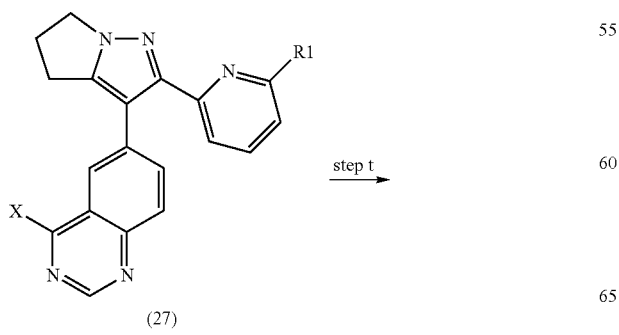

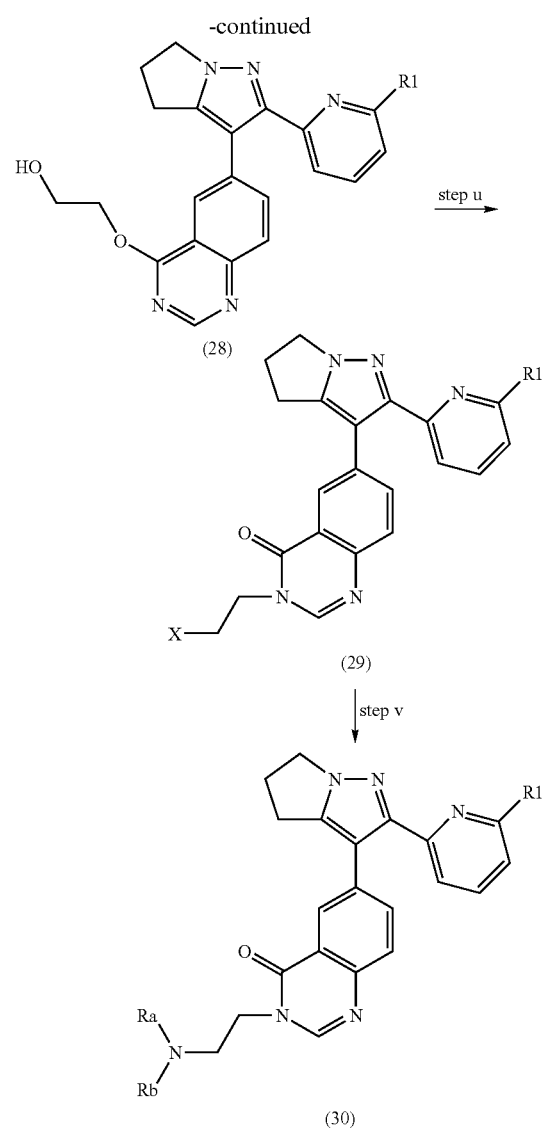

Scheme VI, step t, depicts the displacement of a haloquinazoline of formula (27) to give an alcohol of formula (28). Typically, a compound of formula (27) is contacted with ethylene glycol in the presence of a suitable base such as potassium bis(trimethylsilyl)amide, lithium diisopropylamine, lithium bis(trimethylsilyl)amide, sodium bis(trimethylsilyl)amide, lithium hydride, potassium hydride, sodium alkoxides (sodium methoxide, or sodium ethoxide) or potassium alkoxides (potassium methoxide, or potassium ethoxide), or preferably sodium hydride in a suitable solvent such as tetrahydrofuran, or preferably N,N-dimethylformamide, at temperatures of about −50° C. to ambient temperature. The product, formula (28), can be isolated and purified by techniques well known in the art, such as precipitation, filtration, extraction, evaporation, trituration, chromatography, and recrystallization.

Scheme VI, step u, depicts the conversion of a compound of formula (28) to a compound of formula (29). This conversion is known in the art (Heterocycles (1987), 26(12), 3211-20). Typically, a compound of formula (28) is contacted with a reagent such as phosphorus oxychloride, thionyl chloride, toluenesulfonyl chloride, or preferably methansulfonyl chloride in the presence of a suitable base such as triethylamine, N,N-diisopropylethylamine, or preferably pyridine in an appropriate solvent such as dichloromethane, tetrahydrofuran, N,N-dimethylformamide, or preferably pyridine at temperatures of about −50° C. to ambient temperature. The product of formula (29) can be isolated by methods described above.

Scheme VI, step v, depicts the nucleophilic substitution of leaving group X, by a nucleophile to form a compound of the formula (30). Nucleophilic substitution is well known and appreciated in the art (March, J., *Advanced Organic Chemistry*, copyright 1985, John Wiley and Sons, Inc., pp 255-446). Typically, the compound of formula (29) is reacted with a nucleophile which is typically, but not limited to, secondary amines. The reaction is carried out in a suitable solvent, such as tetrahydrofuran, N,N-dimethylformamide, dimethylsulfoxide, dimethyl acetamide or toluene, preferably N,N-dimethylformamide at temperatures of about 0 to 100° C. The products can be isolated and purified by techniques described above.

SCHEME VII:

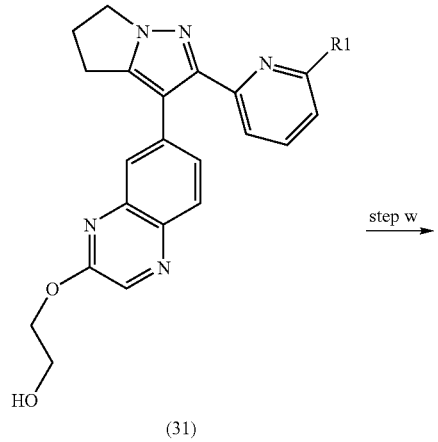

(31)

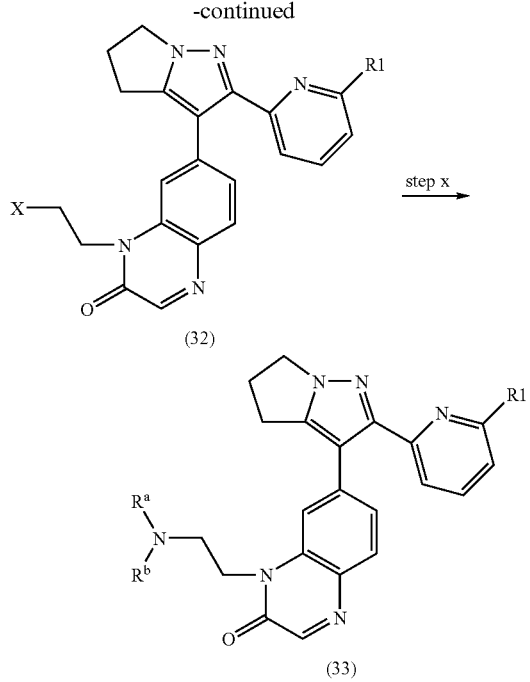

Scheme VII, step w, depicts the conversion of a compound of formula (31) to a compound of formula (32). This conversion is known in the art (Heterocycles (1987), 26(12), 3211-20). Typically, a compound of formula (31) is contacted with a reagent such as phosphorous oxychloride, thionyl chloride, toluenesulfonyl chloride, or preferably methansulfonyl chloride in the presence of a suitable base such as triethylamine, N,N-diisopropylethylamine, or preferably pyridine in an appropriate solvent such as dichloromethane, tetrahydrofuran, N,N-dimethylformamide, or preferably pyridine at temperatures of about −50° C. to ambient temperature. The product of formula (32) can be isolated by methods described above.

Scheme VII, step x, depicts the nucleophilic substitution of leaving group X, by a nucleophile to form a compound of the formula (33). Nucleophilic substitution is well known and appreciated in the art (March, J., *Advanced Organic Chemistry*, copyright 1985, John Wiley and Sons, Inc., pp 255-446). Typically, the compound of formula (32) is reacted with a nucleophile which is typically, but not limited to, secondary amines. The reaction is carried out in a suitable solvent, such as tetrahydrofuran, N,N-dimethylformamide, dimethylsulfoxide, dimethyl acetamide or toluene, preferably N,N-dimethylformamide at temperatures of about 0 to 100° C. The products can be isolated and purified by techniques described above.

The skilled artisan will also appreciate that not all of the substituents in the compounds of Formula (I) will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical.

The skilled artisan will appreciate that the compounds of Formula (I) may be formed into acid addition salts using pharmaceutically acceptable acids. The formation of acid-addition salts is well known and appreciated in the art.

The following preparations and examples further illustrate the preparation of compounds of the present invention and should not be interpreted in any way as to limit the scope. Those skilled in the art will recognize that various modifications may be made while not departing from the spirit and scope of the invention. All publications mentioned in the specification are indicative of the level of those skilled in the art to which this invention pertains.

Preparation 1

6-Iodo-3-methyl-3H-quinazolin-4-one

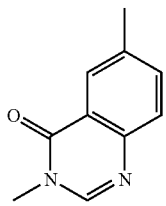

A. Preparation of 6-Iodo-3H-quinazolin-4-one

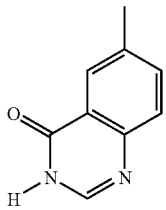

Reflux 2-amino-5-iodo-benzoic acid (Aldrich; 10 g, 38 mmol) in formamide (30 mL) at 120° C. for 18 h. Upon cooling to room temperature, the product is crystallized from the solvent. The product is collected via filtration and the resulting crystals are washed with ether providing the desired 9.2 g (89%) of the titled compound as a pale solid. MS ES+ m/e 273.0 (M+1).

B. Preparation of 6-Iodo-3-methyl-3H-quinazolin-4-one

Suspend sodium hydride (1.13 g, 47 mmol) in a solution of 6-iodo-3H-quinazolin-4-one (2.5 g, 9.2 mmol) in DMF. Stir at room temperature for 20 min, add iodomethane (6.6 g, 46 mmol) into the mixture and stir for 2 h. Dilute the mixture with 3:1 chloroform/isopropyl alcohol and wash with saturated sodium chloride solution. Dry the organic phase (sodium sulfate) and concentrate in vacuo. Purify the residue with flash chromatography (dichloromethane to dichloromethane/methanol) to give 2.5 g (95%) of the titled compound as a white solid. MS ES+ m/e 287 (M+1).

Preparation 2

2-[6-Methyl-(pyridin-2-yl)]-5,6-dihydro-4H-pyrrolo[1,2-b]pyrazole-3-boronic Acid

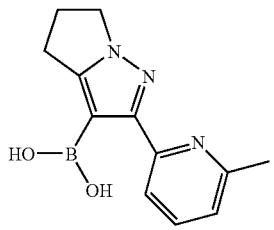

A. Preparation of 3-(6-Methyl-pyridin-2-yl)-3-oxo-propionic Acid Ethyl Ester

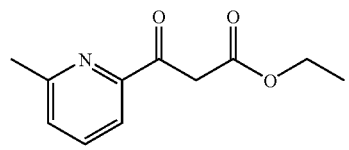

Stir a mixture of sodium ethoxide (90 g, 1.32 mol), toluene (0.5 L), and ethyl acetate (0.2 L, 1.98 mol) in a 2 L flask equipped with reflux condenser, mechanical stirrer, and nitrogen inlet. After 1 h, add 6-methyl-pyridine-2-carboxylic acid methyl ester (Cheung, Y, *Tetrahedron Lett.* 1979, 40, 3809-10; 100 g, 0.66 mol). Heat the mixture at reflux (92° C.) for 20 h. Cool the mixture to room temperature and acidify with glacial acetic acid to pH 6. Wash the resulting gel with water (0.5 L). Separate the layers and extract the aqueous layer with toluene (1×0.5 L) Dry the combined organic layers (sodium sulfate), filter, and concentrate in vacuo to yield the subtitled product (154 g) as a dark oil in 86% purity by HPLC analysis. MS ES+ m/e 208 (M+1).

B. Preparation of 3-[6-Methyl-(pyridin-2-yl)]-3-(2-oxo-pyrrolidin-1-ylimino)-propionic Acid Ethyl Ester

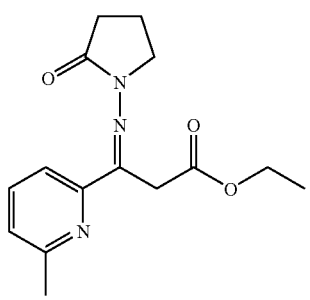

Add 1-aminopyrrolidin-2-one hydrochloride (Zubek, A. Z. *Chem.* 1969, 9(2), 58; 99.4 g, 0.73 mol) to a 3 L flask equipped with mechanical stirrer and nitrogen inlet. Add 3-[6-methyl-(pyridin-2-yl)]-3-oxo-propionic acid ethyl ester (154 g, 0.66 mol), and pyridine (280 mL). Stir the reaction mixture at room temperature for 20 h. Dilute the mixture with water (200 mL) and extract with toluene (2×250 mL). Combine the organic layers, filter, and concentrate in vacuo to yield the subtitled product (201 g) as a dark oil. MS ES+ m/e 290 (M+1).

C. Preparation of 2-[6-Methyl-(pyridin-2-yl)]-5,6-dihydro-4H-pyrrolo[1,2-b]pyrazole-3-carboxylic Acid

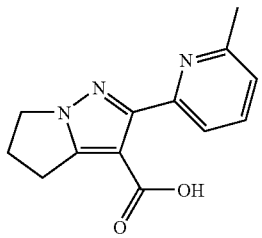

Add sodium ethoxide (90 g, 1.32 mol), toluene (5 L) and 3-[6-methyl-(pyridin-2-yl)]-3-(2-oxo-pyrrolidin-1-ylimino)-propionic acid ethyl ester (Preparation 2-B; 201 g, 0.661 mol) to a 22 L flask equipped with a mechanical stirrer, nitrogen inlet and a reflux condenser. Heat the mixture at 100° C. for 24 h then cool to room temperature. Add water (4 L) and adjust the pH to 4 with concentrated hydrochloric acid. Separate the organic layer and extract the aqueous portion with 10% isopropyl alcohol in chloroform (3×4.5 L). Combine the organic layers, dry (sodium sulfate), filter, and concentrate in vacuo to yield the subtitled product 138 g (86%) as a yellow solid in 78% purity by HPLC analysis. MS ES+ m/e 244 (M+1).

D. Preparation of 3-Bromo-2-[6-methyl-(pyridin-2-yl)]-5,6-dihydro-4H-pyrrolo[1,2b]pyrazole

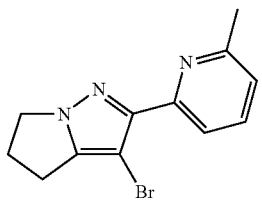

To a solution of 2-[6-methyl-(pyridin-2-yl)]-5,6-dihydro-4H-pyrrolo[1,2-b]pyrazole-3-carboxylic acid (1.4 g, 5.8 mmol) in N,N-dimethylformamide (20 mL) with N-bromosuccinamide (1 g, 5.6 mmol) and stir at room temperature for 16 h. Dilute the mixture with ethyl acetate and wash three times with water, once with brine, dry (sodium sulfate), filter, and concentrate in vacuo to yield 1.5 g (94%) of the title compound as light yellow solid. MS ES+ m/e 278 (M+1).

E. Preparation of 2-[6-Methyl-(pyridin-2-yl)]-5,6-dihydro-4H-pyrrolo[1,2-b]pyrazole-3-boronic Acid Place tetrahydrofuran (28.0 mL) in a 100 mL round-bottom flask equipped with a temperature probe, a magnetic stirrer, and a septum and put under a nitrogen atmosphere. Add 3-bromo-2-[6-methyl-(pyridin-2-yl)]-5,6-dihydro-4H-pyrrolo[1,2-b]pyrazole (1.44 g, 5.18 mmol) and triisopropyl borate (3.10 mL, 13.5 mmol). Cool the mixture to −78° C. using a dry ice/acetone bath. Add 1.4M n-butyllithium in hexanes (8.80 mL, 12.4 mmol) dropwise via a syringe pump over 10 min keeping the temperature below −40° C. Remove the dry ice/acetone bath and allow the reaction mixture to warm to room temperature. Add saturated aqueous ammonium chloride (10 mL) and extract with chloroform (2×100 mL). Combine the organic layers, dry over solid sodium chloride, and remove the solvent under reduced pressure to afford an oil. Purify the oil by normal phase flash chromatography (120 g Biotage KP-Sil 40L: 100% ethyl acetate in hexanes for 25 min, 0-10% methanol in ethyl acetate in ramp over 15 min, then 10% methanol in ethyl acetate) to yield 910 mg (73%) of the title compound. MS ES+ m/e 244 (M+1).

Preparation 3

2-(Pyridin-2-yl)-5,6-dihydro-4H-pyrrolo[1,2-b]pyrazole-3-boronic Acid

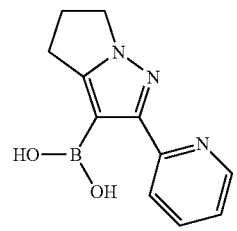

A. Preparation of 3-Oxo-3-(pyridin-2-yl)-propionic Acid Ethyl Ester

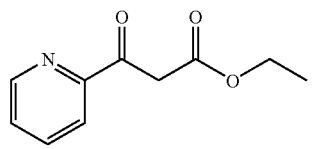

Stir a mixture of sodium ethoxide (360 g, 5.29 mol), toluene (4 L), ethanol (18 mL, 0.265 mol), and ethyl acetate (1.04 L, 10.6 mol) in a 22 L flask equipped with a reflux condenser, nitrogen inlet, and mechanical stirrer. Stir for 1 h as the mixture warms to 26° C. Add pyridine-2-carboxylic acid ethyl ester (Fluka; 400 g, 2.65 mol) and heat the mixture to reflux (90° C.) for 18 h. Cool the mixture to room temperature, dilute with toluene (8 L), wash with water (6 L), and separate the layers. Acidify the aqueous layer to pH 5 with glacial acetic acid. Extract with ethyl acetate (2×4 L), dry the combined organic layers (sodium sulfate), filter, and concentrate in vacuo to yield 466 g (91%) the subtitled compound as a dark oil in 93% purity by HPLC analysis. MS ES+ m/e 194 (M+1).

B. Preparation of 3-(2-Oxo-pyrrolidin-1-ylimino)-3-(pyridin-2-yl)-propionic Acid Ethyl Ester

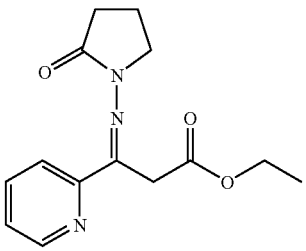

Place 1-aminopyrrolidin-2-one hydrochloride (Zubek, A. Z. *Chem.*, 1969, 9(2), 58; 155.6 g, 1.14 mol) in a 3 L flask equipped with mechanical stirrer and nitrogen inlet. Add 3-oxo-3-pyridin-2-yl-propionic acid ethyl ester (Preparation 3-A; 200 g, 1.04 mol) and pyridine (400 mL). Stir the reaction mixture at room temperature for 20 h. Dilute the mixture with water (500 mL) and extract with toluene (2×500 mL). Combine the organic layers, dry (sodium sulfate), filter, and concentrate in vacuo to yield 280 g (98%) of the subtitled compound as a dark oil. MS ES+ m/e 276 (M+1).

C. Preparation of 2-(Pyridin-2-yl)-5,6-dihydro-4H-pyrrolo[1,2-b]pyrazole-3-Carboxylic Acid

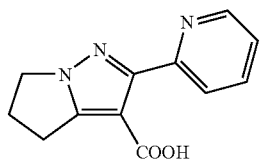

Add sodium ethoxide (145 g, 2.03 mol), followed by toluene (7 L) and 3-(2-oxo-pyrrolidin-1-ylimino)-3-pyridin-2-yl-propionic acid ethyl ester (Preparation 3-B; 280 g, 1.02 mol) to a 22 L flask equipped with mechanical stirrer, nitrogen inlet and a reflux condenser. Heat the mixture to 100° C. for 21 h. Cool to room temperature, add water (6 L), and adjust to pH 5 with concentrated hydrochloric acid. Separate the organic layer and extract the aqueous layer with 10% isopropyl alcohol in chloroform (2×9 L). Combine the organic layers, dry (sodium sulfate), filter, and concentrate in vacuo to yield 218 g (93%) of the title compound as a yellow solid MS ES+ m/e 230 (M+1).

D. Preparation of 3-Bromo-2-(pyridin-2-yl)-5,6-dihydro-4H-pyrrolo[1,2-b]pyrazole

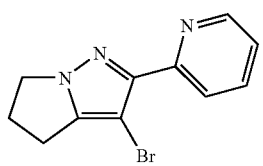

Stir a mixture of 2-(pyridin-2-yl)-5,6-dihydro-4H-pyrrolo[1,2-b]pyrazole-3-carboxylic acid (2 g, 8.7 mmol), sodium bicarbonate (3.3 g, 38.4 mmol), and N-bromosuccinamide (1.7 g, 9.6 mmol) in DMF (50 mL) at room temperature for 2 h. Dilute the crude mixture with water (50 mL) and ethyl acetate (100 mL). Separate the ethyl acetate layer, extract with saturated sodium chloride solution, dry over anhydrous sodium sulfate, filter, and evaporate to a solid mass. Purify by MPLC (SiO$_2$, 1:1 ethyl acetate/hexane) to obtain 1.62 g (70%) of the title compound as a cream solid. MS ES+ m/e 264 (M+1), MS ES+ m/e 266 (M+2).

E. Preparation of 2-(Pyridin-2-yl)-5,6-dihydro-4H-pyrrolo[1,2-b]pyrazole-3-boronic Acid Place tetrahydrofuran (60.0 mL) in a 100 mL round-bottom flask equipped with a temperature probe, a magnetic stirrer, and a septum and put under a nitrogen atmosphere. Add 3-bromo-2-(pyridin-2-yl)-5,6-dihydro-4H-pyrrolo[1,2-b]pyrazole (Preparation 3-D; 3.00 g, 11.4 mmol) and triisopropyl borate (6.80 mL, 29.5 mmol). Cool the mixture to −78° C. using a dry ice/acetone bath. Add 1.41M n-butyllithium in hexanes (19.3 mL, 27.3 mmol) dropwise via a syringe pump over 10 min keeping the temperature below −40° C. Remove the dry ice/acetone bath and allow the reaction mixture to warm to room temperature. Add saturated aqueous ammonium chloride (20 mL) and extract with chloroform (2×150 mL). Combine the organic layers, dry over solid sodium chloride, and remove the solvent under reduced pressure to afford an oil. Purify by normal phase flash chromatography (120 g Biotage KP-Sil 40L: ethyl acetate for 25 min, 0-10% methanol in ethyl acetate in ramp over 15 min, then 10% methanol in ethyl acetate) to obtain 1.43 g (55%) of the title product. MS ES+ m/e 230 (M+1).

Preparation 4

General Suzuki Coupling Procedures

Combine the appropriate heteroarylboronic acid with the appropriate heteroaryl halide (1.2 equiv) in the presence of a suitable palladium catalyst ([1,1']-bis(diphenylphosphino)ferrocene)dichloropalladium(II) (dppf Pd), tetrakis(triphenylphosphine)palladium (0) (tetrakis Pd), or tris(dibenzylideneacetone)dipalladium(0) (Pd$_2$(dba)$_3$), 3-5% mol), a suitable ligand, preferably biphenyl-2-yl-di-tert-butyl-phosphane (6-10% mol), and a suitable base, preferably sodium carbonate (2.0 equiv-3.0 equiv) in dioxane, 4:1 dioxane/ethanol, or 1:1 DMSO/water in a 10 mL glass tube. Seal the reaction vessel with a septum and place in the microwave reactor. Use microwave irradiation to raise the temperature between 80-130° C. over 10-30 min. Alternatively, the tube is placed into a conventional oil bath and heated for 10-30 minutes at 110-140° C. Dilute the reaction mixture with chloroform/isopropyl alcohol and wash the solution with saturated sodium chloride solution. Dry the mixture solution over sodium sulfate and evaporate the solvents to give a viscous mixture. Purify the crude product with flash chromatography by using dichloromethane-10:1 dichloromethane/methanol or dichloromethane-4:1 dichloromethane/tetrahydrofuran-10:1 dichloromethane/methanol as gradient-eluting solvents to give the desired compounds.

Preparation 5

7-Bromo-1-methyl-1H-quinoxalin-2-one

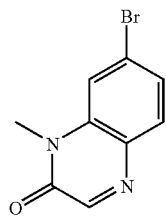

In a procedure analogous to Preparation 1-B, 7-bromo-1H-quinoxalin-2-one (Linda, P. and Marino, G. *Ric. Sci. Rend., Ser. A.* 1963, 3, 225 and Lumma, W. C. et al. *J. Med. Chem.* 1981, 24, 93-101) gives the title compound. MS ES$^+$ m/e 239 (M+1).

Preparation 6

2-{6-[2-[6-Methyl-(pyridin-2-yl)]-5,6-dihydro-4H-pyrrolo[1,2-b]pyrazol-3-yl]-quinazolin-4-yloxy-ethanol

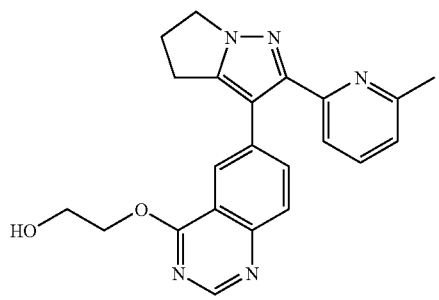

Combine 3-boronic acid-2-[6-methyl-(pyridin-2-yl)]-5,6-dihydro-4H-pyrrolo[1,2-b]pyrazole (Preparation 2; 70 mg, 0.3 mmol) with 4-chloro-6-iodo-quinazoline (Davos Chemicals; 130 mg, 0.45 mmol) in the presence of Pd(dppf)$_2$Cl$_2$ (7 mg, 3% mol), biphenyl-2-yl-di-tert-butyl-phosphane (3 mg, 6% mol), 2M sodium carbonate (1 mL), and 2:1 dioxane/ethylene glycol (6 mL) in a 10 mL glass tube. Seal the tube with a septum and place in a microwave reactor. Use microwave irradiation to raise the temperature to 120° C. over 25 min. Dilute the reaction mixture with 1:1 chloroform/isopropyl alcohol and wash the resulting solution with brine. Dry the mixture (sodium sulfate), filter, and evaporate the solvents to give a viscous mixture. Purify the crude product with flash chromatography using dichloromethane to 1:1 dichloromethane/methanol as gradient eluting solvents to give 80 mg (72%) of the desired compound. MS ES$^+$ m/e 388.2 (M+1).

Preparation 7

1-(2-Chloro-ethyl)-7-[2-[6-methyl-(pyridin-2-yl)]-5,6-dihydro-4H-pyrrolo[1,2-b]pyrazol-3-yl]-1H-quinoxalin-2-one

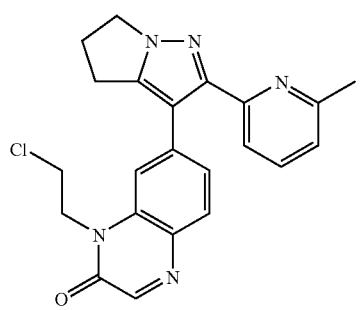

A. Preparation of 7-Bromo-2-chloroquinoxaline

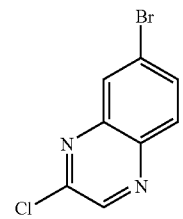

Heat 1,2-diaminobenzene (7.5 g, 69 mmol) and oxoacetic acid ethyl ester (20 mL) in ethanol (100 mL) at 120° C. for 18 h. Cool the mixture and filter the resulting crystals. Wash the crystals with ether and dry. Dissolve the crystals in acetic acid (300 mL), add bromine (5 mL), and stir for 1 h. Filter the resulting crystals, wash with ether, and reflux in POCl$_3$ (30 mL) for 18 h. Remove the solvent in vacuo, dilute with 3:1 chloroform/isopropyl alcohol, and wash with the resulting solution with saturated sodium bicarbonate solution. Dry the organic layer (sodium sulfate), filter, concentrate in vacuo, and purify the residue by silica gel chromatography (dichloromethane to 10% methanol/90% dichloromethane) to afford 4.5 g (58%) of the titled compound as a yellow solid. MS ES$^+$ m/e 245 (M+1).

B. Preparation of 2-(7-Bromoquinoxalin-2-yloxy)-ethanol

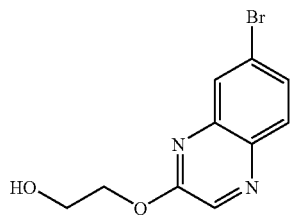

Suspend sodium hydride (310 mg, 13 mmol) in a solution of ethylene glycol (800 mg, 13 mmol) in DMF (50 mL)

previously cooled to 0° C. Allow the mixture to warm to room temperature and stir for 30 min. Add 7-bromo-2-chloroquinoxaline (610 mg, 2.5 mmol) and stir the resulting mixture for 2 h at room temperature. Dilute the mixture with 3:1 chloroform/isopropyl alcohol and wash the resulting solution with saturated sodium chloride solution. Dry and concentrate the organic phase in vacuo and purify the residue via silica gel chromatography to provide 564 mg (85%) of the titled compound. MS ES+ m/e 268 (M+1). $^1$H NMR (400 MHz, CDCl$_3$) δ 8. (s, 1H), 8.0 (d, J=2.0 Hz, 1H), 7.90 (dd, J=8.8, 2.0 Hz, 1H), 7.7 (d, J=8.8 Hz, 1H), 4.6 (t, J=4.8 Hz, 2H), 4.39 (t, J=4.8 Hz, 2H).

C. Preparation of 2-{7-[2-[6-Methyl-(pyridin-2-yl)]-5,6-dihydro-4H-pyrrolo[1,2-b]pyrazol-3-yl]-quinoxalin-2-yloxy}-ethanol

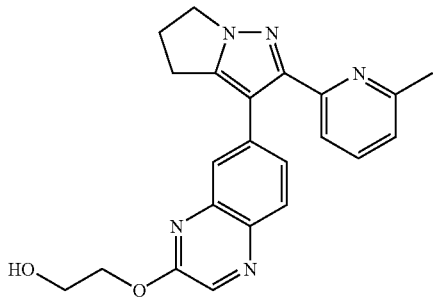

Combine 3-boronic acid-2-[6-methyl-(pyridin-2-yl)]-5,6-dihydro-4H-pyrrolo[1,2-b]pyrazole (Preparation 2; 110 mg, 0.45 mmol) with 2-(7-bromo-quinoxalin-2-yloxy)-ethanol (80 mg, 0.3 mmol) in the presence of Pd(dppf)$_2$Cl$_2$ (12 mg, 3 mol %), biphenyl-2-yl-di-tert-butyl-phosphane (6 mg, 6 mol %), and 2 M sodium carbonate solution (1 ml) in dioxane (5 ml) in a 10 ml glass tube. Seal the tube with a septum and place in a microwave reactor. Use microwave irradiation to raise the temperature to 100° C. over 15 min. Dilute the reaction mixture with 1:1 chloroform/isopropyl alcohol and wash the resulting solution with brine. Dry the organic solution (sodium sulfate), filter, and evaporate the solvents to give a viscous residue. Purify the residue by silica gel chromatography (dichloromethane to 1:1 dichloromethane/methanol) to give 87 mg (75%) of the titled desired compound. MS ES+ 388.2 (M+1).

D. Preparation of 1-(2-Chloro-ethyl)-7-[2-[6-methyl-(pyridin-2-yl)]-5,6-dihydro-4H-pyrrolo[1,2-b]pyrazol-3-yl]-1H-quinoxalin-2-one Cool a solution of 2-{7-[2-[6-methyl-(pyridin-2-yl)]-5,6-dihydro-4H-pyrrolo[1,2-b]pyrazol-3-yl]-quinoxalin-2-yloxy}-ethanol (0.5 g, 1.3 mmol) and diisopropylamine (0.5 ml) in dry dichloromethane (10 mL) to −30° C. Add methanesulfonylchloride (0.5 ml) dropwise to the solution and stir the resulting mixture for 30 min while allowing the reaction mixture to warm to room temperature. Add 5 N hydrochloric acid (0.2 mL) and pyridine (1 mL) to the mixture and heat at 80° C. for 3 h. Dilute the reaction mixture with 1:1 chloroform/isopropyl alcohol and wash the solution with saturated sodium chloride solution. Dry the organic layer (sodium sulfate), filter, and evaporate the solvents. Purify the residue by silica gel chromatography (dichloromethane to 1:1 dichloromethane/methanol) to give 274 mg (68%) of the titled compound. MS ES+ 407 (M+1).

Using the Suzuki coupling procedure as described in Preparation 4, the following final products are obtained:

| Example | Product | Starting Material A | Starting Material B | Physical Data | Comments Suzuki Conditions |
|---|---|---|---|---|---|
| 1 | 3-Methyl-6-[2-[6-methyl-(pyridin-2-yl)]-5,6-dihydro-4H-pyrrolo[1,2-b]pyrazol-3-yl]-3H-quinazolin-4-one | Preparation 1 | Preparation 2 | MS ES+ m/e 358 (M + 1) | Tetrakis Pd, DMSO/water |

-continued

| Example | Product | Starting Material A | Starting Material B | Physical Data | Comments Suzuki Conditions |
|---|---|---|---|---|---|
| 2 | 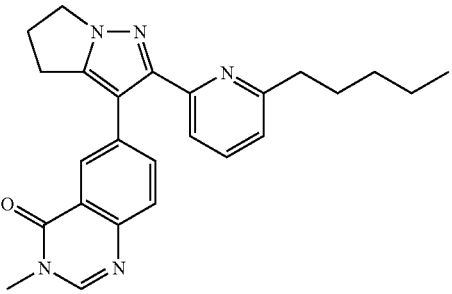<br>3-Methyl-6-[2-[6-pentyl-(pyridin-2-yl)]-5,6-dihydro-4H-pyrrolo[1,2-b]pyrazol-3 yl]-3H-quinazolin-4-one | Preparation 1 | 2-[6-Pentyl-(pyridin-2-yl)]-5,6-dihydro-4H-pyrrolo[1,2-b]pyrazole-3-boronic Acid: a by-product from Preparation 2, not isolated. | MS ES+ m/e 414 (M + 1) | Tetrakis Pd, DMSO/water |
| 3 | 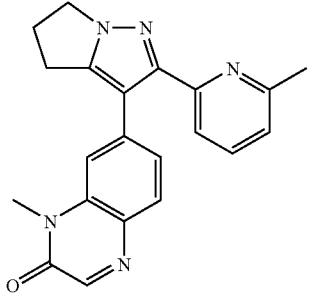<br>1-Methyl-7-[2-[6-methyl-(pyridin-2-yl)]-5,6-dihydro-4H-pyrrolo[1,2-b]pyrazol-3-yl]-1H-quinoxalin-2-one | Preparation 5 | Preparation 2 | MS ES+ m/e 358.2 (M + 1) | Dppf Pd, Dioxane/ethanol |
| 4 | 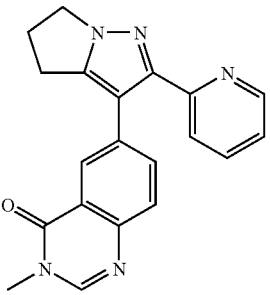<br>3-Methyl-6-[2-(pyridin-2-yl)-5,6-dihydro-4H-pyrrolo[1,2-b]pyrazol-3-yl]-3H-quinazolin-4-one | Preparation 1 | Preparation 3 | MS ES+ m/e 344 (M + 1) | Tetrakis Pd, DMSO/water |

| Example | Product | Starting Material A | Starting Material B | Physical Data | Comments Suzuki Conditions |
|---|---|---|---|---|---|
| 5 | 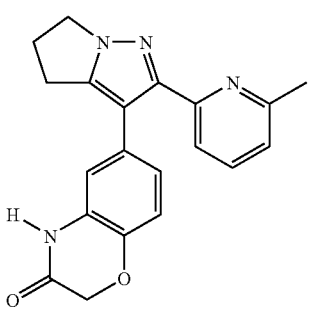<br>6-[2-[6-Methyl-(pyridin-2-yl)]-5,6-dihydro-4H-pyrrolo[1,2-b]pyrazol-3-yl]-4H-benzo[1,4]oxazin-3-one | 6-Bromo-4H-benzo[1,4]oxazin-3-one (Int. Pat. Appl. W003097639 A1) | Preparation 2 | MS ES+ m/e 347 (M + 1) | Tetrakis Pd, dioxane/water |

EXAMPLE 6

3-(2-Chloro-ethyl)-6-[2-[6-methyl-(pyridin-2-yl)]-5,6-dihydro-4H-pyrrolo[1,2-b]pyrazol-3-yl]-3H-quinazolin-4-one (Preparation YW14)

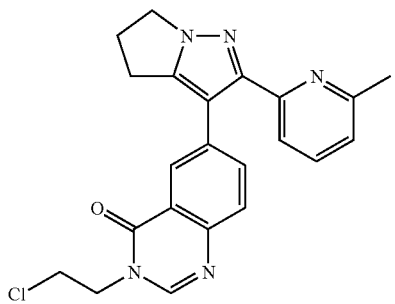

Dissolve 2-{7-[2-[6-methyl-(pyridin-2-yl)]-5,6-dihydro-4H-pyrrolo[1,2-b]pyrazol-3-yl]-quinoxalin-2-yloxy}-ethanol (Preparation 6; 300 mg, 0.8 mmol) in dry pyridine (5 mL). After cooling the solution to −20° C. add methane sulfonyl chloride (1 mL). Stir the resulting mixture at −20° C. for 10 min, then at room temperature for 30 min. Dilute the reaction mixture with 1:1 chloroform/isopropyl alcohol. Wash the mixture with saturated sodium chloride solution, separate the organic solvent, and concentrate in vacuo at 50° C. Purify the crude product with silica gel chromatography to give 280 mg (89%) of the target compound. MS ES+ m/e 405.1 (M+1). $^1$H NMR (400 MHz, CDCl$_3$) δ 8.3 (d, J=1.6 Hz, 1H), 8.0 (s, 1H), 7.7 (dd, J=8.4, 2 Hz, 1H), 7.6 (d, J=8.4 Hz, 1H), 7.5 (t, J=7.6 Hz, 1H), 7.3 (m, 1H), 7.0 (m, 1H), 4.3 (m, 4H), 3.9 (t, J=5.6 Hz, 2H), 3.1 (m, 4H), 2.7 (m, 2H), 2.5 (s, 3H).

EXAMPLE 7

6-[2-[6-Methyl-(pyridin-2-yl)]-5,6-dihydro-4H-pyrrolo[1,2-b]pyrazol-3-yl]-3-(2-morpholin-4-yl-ethyl)-3H-quinazolin-4-one

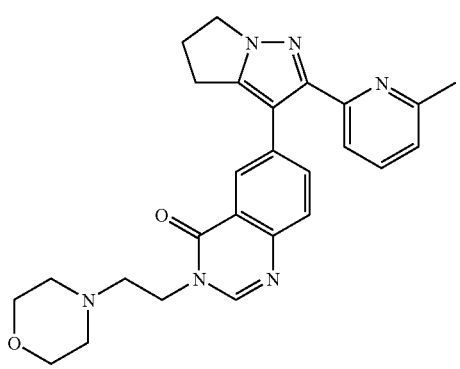

Combine 3-(2-chloro-ethyl)-6-[2-[6-methyl-(pyridin-2-yl)]-5,6-dihydro-4H-pyrrolo[1,2-b]pyrazol-3-yl]-3H-quinazolin-4-one (Example 6; 30 mg, 0.07 mmol) and morpholine (1 mL) in a pressure tube. Seal the tube and place in a microwave reactor. Radiate the mixture and heat at 140° C. for 1 h. The crude product is purified with silica gel chromatography, using dichloromethane to 10:1 dichloromethane/methanol as eluting solvents to give 25 mg (74%) of the target compound. MS ES+ m/e 457.5 (M+1). $^1$H NMR (400 MHz, CD$_2$Cl$_2$) δ 8.3 (d, J=2.0 Hz, 1H), 8.0 (s, 1H), 7.7 (dd, J=8.0, 2 Hz, 1H), 7.6 (m, 2H), 7.5 (d, J=7.6 Hz, 1H), 7.0 (d, J=8 Hz, 1H), 4.3 (t, J=7.2 Hz, 2H), 4.1 (t, J=5.6 Hz, 2H), 3.6 (m, 4H), 3.1 (t, J=6.8 Hz, 2H), 2.7 (m, 4H), 2.5 (m, 4H), 2.4 (s, 3H).

Using the alkylation procedure as described in Example 7, the following final products are obtained:

| Example | Product | Starting Material A | Starting Material B | Physical Data |
|---|---|---|---|---|
| 8 | 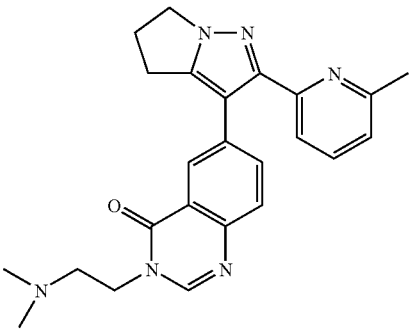<br>3-(2-Dimethylamino-ethyl)-6-[2-[6-methyl-(pyridin-2-yl)]-5,6-dihydro-4H-pyrrolo[1,2-b]pyrazol-3-yl]-3H-quinazolin-4-one | Example 6 | N,N-Di-methylamine | MS ES+ m/e 415.2 (M + 1) |
| 9 | 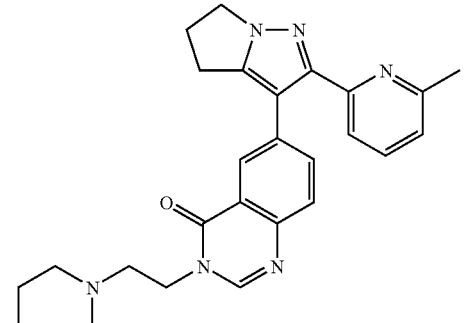<br>6-[2-[6-Methyl-(pyridin-2-yl)]-5,6-dihydro-4H-pyrrolol[1,2-b]pyrazol-3-yl]-3-(2-piperidin-1-yl-ethyl)-3H-quinazolin-4-one | Example 6 | Piperidine | MS ES+ m/e 455.2 (M + 1) |
| 10 | 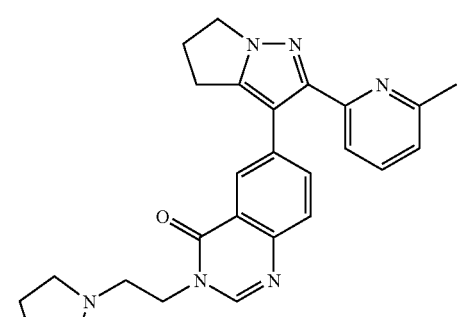<br>6-[2-[6-Methyl-(pyridin-2-yl)]-5,6-dihydro-4H-pyrrolo[1,2-b]pyrazol-3-yl]-3-(2-pyrrolidin-1-yl-ethyl)-3H- | Example 6 | Pyrrolidine | MS ES+ m/e 441.1 (M + 1) |

-continued

| Example | Product | Starting Material A | Starting Material B | Physical Data |
|---|---|---|---|---|
| 11 | quinazolin-4-one<br>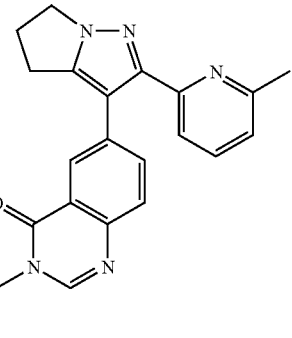<br>3-(2-Azepan-1-yl-ethyl)-6-[2-[6-methyl-(pyridin-2-yl)]-5,6-dihydro-4H-pyrrolo[1,2-b]pyrazol-3-yl]-3H-guinazolin-4-one | Example 6 | Azepane | MS ES+ m/e 469.2 (M + 1) |

EXAMPLE 12

Preparation of 7-[2-[6-Methyl-(pyridin-2-yl)]-5,6-dihydro-4H-pyrrolo[1,2-b]pyrazol-3-yl]-1-[2-(pyrrolidin-1-yl)-ethyl]-3,4-dihydro-1H-quinoxalin-2-one

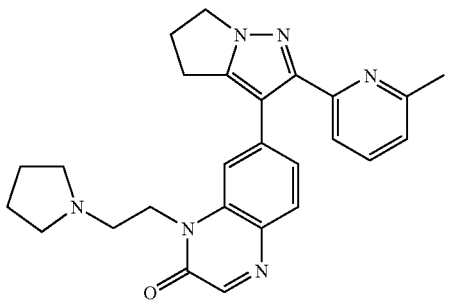

Combine 1-(2-chloro-ethyl)-7-[2-[6-methyl-(pyridin-2-yl)]-5,6-dihydro-4H-pyrrolo[1,2-b]pyrazol-3-yl]-1H-quinoxalin-2-one (Preparation 7; 60 mg, 0.15 mmol) and pyrrolidine (0.5 ml) in dioxane (5 mL) in a pressure tube. Seal the tube and heat at 110° C. for 40 min. Dilute the reaction mixture with 1:1 chloroform/isopropyl alcohol and wash the solution with saturated sodium chloride solution. Dry the organic phase (sodium sulfate), filter, and concentrate in vacuo. Purify the residue by silica gel chromatography (dichloromethane to 1:1 dichloromethane/methanol) to give 54 mg (84%) of the titled compound. MS ES+ m/e 441 (M+1).

Using the alkylation procedure as described in Example 12, the following final product is obtained:

| Example | Product | Starting Material A | Starting Material B | Physical Data |
|---|---|---|---|---|
| 13 | 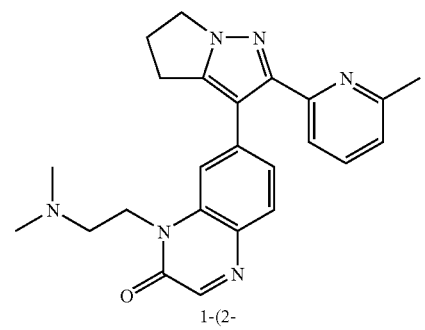<br>1-(2- | Preparation 7 | N,N-Dimethyl-amine | MS ES+ m/e 415.2 (M + 1) |

| Example | Product | Starting Material A | Starting Material B | Physical Data |
|---------|---------|---------------------|---------------------|---------------|
|         | Dimethylamino-ethyl)-7-[2-[6-methyl-(pyridin-2-yl)]-5,6-dihydro-4H-pyrrolo[1,2-b]pyrazol-3-yl]-3,4-dihydro-1H-quinoxalin-2-one | | | |

The compounds disclosed herein were tested by the following protocols for TGF-β inhibition, as described below in the protocol description.

TGF-β Receptor I Purification and In Vitro Kinase Reactions

For TGF-β Type I (RIT204D) Receptors:

The 6×-HIS tagged cytoplasmic kinase domain of each receptor was expressed and purified from Sf9 insect cell lysates as briefly described below:

Cell pellets after 48-72 h of infection were lysed in lysis buffer (LB: 50 mM Tris pH 7.5, 150 mM NaCl, 50 mM NaF, 0.5% NP40 with freshly added 20 mM β-mercaptoethanol, 10 mM imidazole, 1 mM PMSF, 1×EDTA-free Complete Protease Inhibitor (Boehringer Mannheim). Cell lysates were clarified by centrifugation and 0.45 uM filtered prior to purification by Ni/NTA affinity chromatography (Qiagen).

Chromatography Protocol:

Equilibrate with 10 CV of LB, load sample, wash with 10 CV RIPA buffer (50 mM Tris pH 7.5, 150 mM NaCl, 1% NP40, 1 mM EDTA, 0.25% sodium deoxycholate, added fresh 20 mM β-mercaptoethanol, 1 mM PMSF), wash with 10 CV LB, wash with 10 CV 1×KB (50 mM Tris pH 7.5, 150 mM NaCl, 4 mM $MgCl_2$, 1 mM NaF, 2 mM β-mercaptoethanol), elute with a linear gradient of 1×KB containing 200 mM Imidazole. Both enzymes were approximately 90% pure and had autophosphorylation activity. Reactions: 170-200 nM enzyme in 1×KB, compound dilution series in 1×KB/16% DMSO (20 μM to 1 nM final concentration with 4% DMSO final concentration), reactions started by adding ATP mix (4 uM ATP/1 uCi $^{33}$P-γ-ATP final concentrations) in 1×KB.

Reactions were incubated at 30° C. for 1 h. Reactions were stopped and quantitated using standard TCA/BSA precipitation onto Millipore FB glass fiber filter plates and by liquid scintillation counting on a MicroBeta JET.

All the compounds exemplified herein inhibit the TGF-β Type I (RIT204D) receptor kinase domain with $IC_{50}$ values <20 μM.

Conditions "characterized by enhanced TGF-β activity" include those wherein TGF-β synthesis is stimulated so that TGF-β is present at increased levels or wherein TGF-β latent protein is undesirably activated or converted to active TGF-β protein or wherein TGF-β receptors are upregulated or wherein the TGF-β protein shows enhanced binding to cells or extracellular matrix in the location of the disease. Thus, in either case "enhanced activity" refers to any condition wherein the biological activity of TGF-β is undesirably high, regardless of the cause.

A number of diseases have been associated with TGF-β1 over production. Inhibitors of TGF-β intracellular signaling pathway are useful treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post glaucoma drainage surgery are associated with TGF-β1 overproduction.

Fibrotic diseases associated with TGF-β1 overproduction can be divided into chronic conditions such as fibrosis of the kidney, lung and liver and more acute conditions such as dermal scarring and restenosis (Chamberlain, J. Cardiovascular Drug Reviews, 19(4):329-344). Synthesis and secretion of TGF-β1 by tumor cells can also lead to immune suppression such as seen in patients with aggressive brain or breast tumors (Arteaga, et al. (1993) J. Clin. Invest. 92:2569-2576). The course of Leishmanial infection in mice is drastically altered by TGF-β1 (Barral-Netto, et al. (1992) Science 257:545-547). TGF-β1 exacerbated the disease, whereas TGF-β1 antibodies halted the progression of the disease in genetically susceptible mice. Genetically resistant mice became susceptible to Leishmanial infection upon administration of TGF-β1.

The profound effects of TGF-β1 on extracellular matrix deposition have been reviewed (Rocco and Ziyadeh (1991) in Contemporary Issues in Nephrology v.23, Hormones, autocoids and the kidney. ed. Jay Stein, Churchill Livingston, N.Y. pp. 391-410; Roberts, et al. (1988) Rec. Prog. Hormone Res. 44:157-197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGF-β1 has profound effects on the kidney. The accumulation of mesangial matrix in proliferative glomerulonephritis (Border, et al. (1990) Kidney Int. 37:689-695) and diabetic nephropathy (Mauer, et al. (1984) J. Clin. Invest. 74:1143-1155) are clear and dominant pathological features of the diseases. TGF-β1 levels are elevated in human diabetic glomerulosclerosis (advanced neuropathy) (Yamamoto, et al. (1993) Proc. Natl. Acad. Sci. 90:1814-1818). TGF-β1 is an important mediator in the genesis of renal fibrosis in a number of animal models (Phan, et al. (1990) Kidney Int. 37:426; Okuda, et al. (1990) J. Clin. Invest. 86:453). Suppression of experimentally induced glomerulonephritis in rats has been demonstrated by antiserum against TGF-β1 (Border, et al. (1990) Nature 346:371) and by an extracellular matrix protein, decorin, which can bind TGF-β1 (Border, et al. (1992) Nature 360:361-363).

Too much TGF-β1 leads to dermal scar-tissue formation. Neutralizing TGF-β1 antibodies injected into the margins of healing wounds in rats have been shown to inhibit scarring without interfering with the rate of wound healing or the tensile strength of the wound (Shah, et al. (1992) Lancet 339:213-214). At the same time there was reduced angiogenesis, reduced number of macrophages and monocytes in the wound, and a reduced amount of disorganized collagen fiber deposition in the scar tissue.

TGF-β1 may be a factor in the progressive thickening of the arterial wall which results from the proliferation of smooth muscle cells and deposition of extracellular matrix in the artery after balloon angioplasty. The diameter of the restenosed artery may be reduced 90% by this thickening, and since most of the reduction in diameter is due to extracellular matrix rather than smooth muscle cell bodies, it may be possible to open these vessels to 50% simply by reducing extensive extracellular matrix deposition. In uninjured pig arteries transfected in vivo with a TGF-β1 gene, TGF-β1 gene expression was associated with both extracellular matrix synthesis and hyperplasia (Nabel, et al. (1993) Proc. Natl. Acad. Sci. USA 90:10759-10763). The TGF-β1 induced hyperplasia was not as extensive as that induced with PDGF-BB, but the extracellular matrix was more extensive with TGF-β1 transfectants. No extracellular matrix deposition was associated with FGF-1 (a secreted form of FGF) induced hyperplasia in this gene transfer pig model (Nabel (1993) Nature 362:844-846).

There are several susceptible neoplasms that are contemplated for treatment by the present invention. MATLyLu rat prostate cancer cells (Steiner and Barrack (1992) Mol. Endocrinol. 6:15-25) and MCF-7 human breast cancer cells (Arteaga, et al. (1993) Cell Growth and Differ. 4:193-201) became more tumorigenic and metastatic after transfection with a vector expressing the mouse TGF-β1. TGF-β1 has been associated with angiogenesis, metastasis and poor prognosis in human prostate and advanced gastric cancer (Wikstrom, P., et al. (1998) Prostate 37: 19-29; Saito, H. et al. (1999) Cancer 86: 1455-1462). In breast cancer, poor prognosis is associated with elevated TGF-β (Dickson, et al. (1987) Proc. Natl. Acad. Sci. USA 84:837-841; Kasid, et al. (1987) Cancer Res. 47:5733-5738; Daly, et al. (1990) J. Cell Biochem. 43:199-211; Barrett-Lee, et al. (1990) Br. J. Cancer 61:612-617; King, et al. (1989) J. Steroid Biochem. 34:133-138; Welch, et al. (1990) Proc. Natl. Acad. Sci. USA 87:7678-7682; Walker, et al. (1992) Eur. J. Cancer 238:641-644) and induction of TGF-β1 by tamoxifen treatment (Butta, et al. (1992) Cancer Res. 52:4261-4264) has been associated with failure of tamoxifen treatment for breast cancer (Thompson, et al. (1991) Br. J. Cancer 63:609-614). Anti TGF-β1 antibodies inhibit the growth of MDA-231 human breast cancer cells in athymic mice (Arteaga, et al. (1993) J. Clin. Invest. 92:2569-2576), a treatment which is correlated with an increase in spleen natural killer cell activity. CHO cells transfected with latent TGF-β1 also showed decreased NK activity and increased tumor growth in nude mice (Wallick, et al. (1990) J. Exp. Med. 172:1777-1784). Thus, TGF-β secreted by breast tumors may cause an endocrine immune suppression. High plasma concentrations of TGF-β1 have been shown to indicate poor prognosis for advanced breast cancer patients (Anscher, et al. (1993) N. Engl. J. Med. 328:1592-1598). Patients with high circulating TGF-β before high dose chemotherapy and autologous bone marrow transplantation are at high risk for hepatic veno-occlusive disease (15-50% of all patients with a mortality rate up to 50%) and idiopathic interstitial pneumonitis (40-60% of all patients). The implication of these findings is 1) that elevated plasma levels of TGF-β1 can be used to identify at risk patients and 2) that reduction of TGF-β1 could decrease the morbidity and mortality of these common treatments for breast cancer patients.

Many malignant cells secrete transforming growth factor-β (TGF-β), a potent immunosuppressant, suggesting that TGF-β production may represent a significant tumor escape mechanism from host immunosurveillance. Establishment of a leukocyte sub-population with disrupted TGF-β signaling in the tumor-bearing host offers a potential means for immunotherapy of cancer. A transgenic animal model with disrupted TGF-β signaling in T cells is capable of eradicating a normally lethal TGF-β overexpressing lymphoma tumor, EL4 (Gorelik and Flavell, (2001) Nature Medicine 7(10): 1118-1122). Down regulation of TGF-β secretion in tumor cells results in restoration of immunogenicity in the host, while T-cell insensitivity to TGF-β results in accelerated differentiation and autoimmunity, elements of which may be required in order to combat self-antigen-expressing tumors in a tolerized host. The immunosuppressive effects of TGF-β have also been implicated in a subpopulation of HIV patients with lower than predicted immune response based on their CD4/CD8 T cell counts (Garba, et al. J. Immunology (2002) 168: 2247-2254). A TGF-β neutralizing antibody was capable of reversing the effect in culture, indicating that TGF-β signaling inhibitors may have utility in reversing the immune suppression present in this subset of HIV patients.

During the earliest stages of carcinogenesis, TGF-β1 can act as a potent tumor suppressor and may mediate the actions of some chemopreventive agents. However, at some point during the development and progression of malignant neoplasms, tumor cells appear to escape from TGF-β-dependent growth inhibition in parallel with the appearance of bioactive TGF-β in the microenvironment. The dual tumor suppression/tumor promotion roles of TGF-β have been most clearly elucidated in a transgenic system overexpressing TGF-β in keratinocytes. While the transgenics were more resistant to formation of benign skin lesions, the rate of metastatic conversion in the transgenics was dramatically increased (Cui, et al (1996) Cell 86(4):531-42). The production of TGF-β1 by malignant cells in primary tumors appears to increase with advancing stages of tumor progression. Studies in many of the major epithelial cancers suggest that the increased production of TGF-β by human cancers occurs as a relatively late event during tumor progression. Further, this tumor-associated TGF-β provides the tumor cells with a selective advantage and promotes tumor progression. The effects of TGF-β on cell/cell and cell/stroma interactions result in a greater propensity for invasion and metastasis. Tumor-associated TGF-β may allow tumor cells to escape from immune surveillance since it is a potent inhibitor of the clonal expansion of activated lymphocytes. TGF-β has also been shown to inhibit the production of angiostatin. Cancer therapeutic modalities such as radiation therapy and chemotherapy induce the production of activated TGF-β in the tumor, thereby selecting outgrowth of malignant cells that are resistant to TGF-β growth inhibitory effects. Thus, these anticancer treatments increase the risk and hasten the development of tumors with enhanced growth and invasiveness. In this situation, agents targeting TGF-β-mediated signal transduction might be a very effective therapeutic strategy. The resistance of tumor cells to TGF-β has been shown to negate much of the cytotoxic effects of radiation therapy and chemotherapy and the treatment-dependent activation of TGF-β in the stroma may even be detrimental as it can make the microenvironment more conducive to tumor progression and contributes to tissue damage leading to fibrosis. The development of a TGF-β signal transduction inhibitors is likely to benefit the treatment of progressed cancer alone and in combination with other therapies.

The compounds are useful for the treatment of cancer and other disease states influenced by TGF-β by inhibiting TGF-β in a patient in need thereof by administering said compound(s) to said patient. TGF-β would also be useful against atherosclerosis (T. A. McCaffrey: TGF-βs and TGF-β Receptors in Atherosclerosis: Cytokine and Growth Factor Reviews 2000, 11, 103-114) and Alzeheimer's (Masliah, E.; Ho, G.; Wyss-Coray, T.: Functional Role of TGF-β in Alzheimer's Disease Microvascular Injury: Lessons from Transgenic Mice: Neurochemistry International 2001, 39, 393-400) diseases.

Pharmaceutical Compositions

The compositions of the present invention are therapeutically effective amounts of the TGF-β antagonists, noted above. The composition may be formulated with common excipients, diluents or carriers, and compressed into tablets, or formulated elixirs or solutions for convenient oral administration or administered by intramuscular intravenous routes. The compounds can be administered transdermally and maybe formulated as sustained release dosage forms and the like.

The method of treating a human patient according to the present invention includes administration of the TGF-β antagonists. The TGF-β antagonists are formulated into formulations which may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case of parenteral or inhalation administration, and from about 25 to 500 mg in the case of oral or rectal administration) the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations useful for separate administration of the TGF-β antagonists will normally consist of at least one compound selected from the compounds specified herein mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance. Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, for injection, and for oral ingestion.

We claim:

1. A compound of the formula:

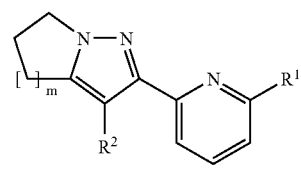

Formula I wherein $R^1$ is hydrogen or $(C_1-C_6)$ alkyl;
$R^2$ is

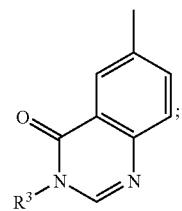

$R^3$ is $(C_1-C_6)$alkyl, or $(CH_2)_nX$;

X is selected from the group consisting of a halogen, $NR^aR^b$,

N-morpholino, N-piperidine, N-pyrrolidine, or N-azepane;

n is an integer from 1-4;

m is an integer from 1-3;

$R^a$ and $R^b$ are each independently hydrogen or $(C_1-C_6)$ alkyl;

and the pharmaceutically acceptable salts thereof.

2. A compound of the formula:

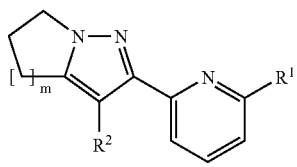

Formula I wherein $R^1$ is hydrogen or $(C_1-C_6)$ alkyl;

$R^2$ is

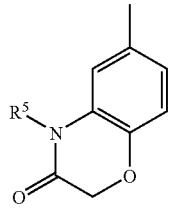

$R^5$ is hydrogen, $(C_1-C_6)$alkyl, or $(CH_2)_nX$;

X is selected from the group consisting of a halogen, $NR^aR^b$,

N-morpholino, N-piperidine, N-pyrrolidine, or N-azepane;

n is an integer from 1-4;

m is an integer from 1-3;

$R^a$ and $R^b$ are each independently hydrogen or $(C_1-C_6)$ alkyl;

and the pharmaceutically acceptable salts thereof.

3. A compound according to claim 1 wherein m is 1.

4. A compound according to claim 2 wherein m is 1.

5. A compound according to claim 1 wherein $R^3$ is methyl.

6. A compound according to claim 1 wherein $R^1$ is methyl.

7. A compound according to claim 2 wherein $R^1$ is methyl.

8. A pharmaceutical formulation comprising a compound according to claim 1 in combination with a pharmaceutically acceptable diluent, excipient or carrier.

9. A pharmaceutical formulation comprising a compound according to claim 2 in combination with a pharmaceutically acceptable diluent, excipient or carrier.

10. A method of treating breast cancer or prostate cancer in a patient in need thereof which comprises administering to said patient a therapeutically effective amount of a compound according to claim 1.

11. A method of treating breast cancer or prostate cancer in a patient in need thereof which comprises administering to said patient a therapeutically effective amount of a compound according to claim 2.

\* \* \* \* \*